(12) United States Patent
Lulla et al.

(10) Patent No.: US 9,446,054 B2
(45) Date of Patent: *Sep. 20, 2016

(54) PHARMACEUTICAL PRODUCTS AND COMPOSITION COMPRISING SPECIFIC ANTICHOLINERGIC AGENTS, β-2 AGONISTS AND CORTICOSTEROIDS

(71) Applicant: Cipla Limited, Mumbai Central (IN)

(72) Inventors: Amar Lulla, Mumbai (IN); Geena Malhotra, Mumbai (IN)

(73) Assignee: Cipla Limited, Mumbai (IN)

( * ) Notice: Subject to any disclaimer, the term of this patent is extended or adjusted under 35 U.S.C. 154(b) by 0 days.

This patent is subject to a terminal disclaimer.

(21) Appl. No.: 14/570,679

(22) Filed: Dec. 15, 2014

(65) Prior Publication Data

US 2015/0098999 A1 Apr. 9, 2015

Related U.S. Application Data

(63) Continuation of application No. 10/525,736, filed as application No. PCT/GB03/03751 on Aug. 29, 2003, now Pat. No. 8,962,601.

(30) Foreign Application Priority Data

Aug. 29, 2002 (GB) .................................. 0220095.4
Nov. 22, 2002 (GB) .................................. 0227342.3

(51) Int. Cl.

| | |
|---|---|
| *A61K 31/56* | (2006.01) |
| *A61K 31/138* | (2006.01) |
| *A61K 31/38* | (2006.01) |
| *A61K 31/381* | (2006.01) |
| *A61K 31/46* | (2006.01) |
| *A61K 31/58* | (2006.01) |
| *A61K 9/00* | (2006.01) |
| *A61K 31/135* | (2006.01) |
| *A61K 31/167* | (2006.01) |
| *A61K 45/06* | (2006.01) |
| *A61K 31/439* | (2006.01) |
| *A61K 9/16* | (2006.01) |
| *A61K 31/137* | (2006.01) |
| *A61K 31/573* | (2006.01) |
| *A61K 47/10* | (2006.01) |
| *A61K 47/12* | (2006.01) |
| *A61K 47/24* | (2006.01) |
| *A61K 47/26* | (2006.01) |

(52) U.S. Cl.
CPC .............. *A61K 31/58* (2013.01); *A61K 9/008* (2013.01); *A61K 9/0075* (2013.01); *A61K 9/0078* (2013.01); *A61K 9/16* (2013.01); *A61K 31/135* (2013.01); *A61K 31/137* (2013.01); *A61K 31/138* (2013.01); *A61K 31/167* (2013.01); *A61K 31/38* (2013.01); *A61K 31/439* (2013.01); *A61K 31/46* (2013.01); *A61K 31/56* (2013.01); *A61K 31/573* (2013.01); *A61K 45/06* (2013.01); *A61K 47/10* (2013.01); *A61K 47/12* (2013.01); *A61K 47/24* (2013.01); *A61K 47/26* (2013.01)

(58) Field of Classification Search
CPC .. A61K 31/56; A61K 31/138; A61K 31/381; A61K 31/46; A61K 9/007
See application file for complete search history.

(56) References Cited

U.S. PATENT DOCUMENTS

| | | |
|---|---|---|
| 6,423,298 B2 | 7/2002 | McNamara et al. |
| 6,645,466 B1 | 11/2003 | Keller et al. |
| 8,962,601 B2 | 2/2015 | Lulla et al. |
| 2002/0099023 A1 | 7/2002 | Boucher, Jr. |
| 2003/0018019 A1 | 1/2003 | Meade et al. |
| 2006/0035874 A1 | 2/2006 | Lulla et al. |

FOREIGN PATENT DOCUMENTS

| | | |
|---|---|---|
| WO | WO-0207672 A2 | 1/2002 |
| WO | WO-03000241 A2 | 1/2003 |

OTHER PUBLICATIONS

"U.S. Appl. No. 10/525,736, Final Office Action mailed Feb. 3, 2012", 18 pgs.
"U.S. Appl. No. 10/525,736, Final Office Action mailed May 5, 2009", 18 pgs.
"U.S. Appl. No. 10/525,736, Final Office Action mailed Sep. 30, 2010", 25 pgs.
"U.S. Appl. No. 10/525,736, Non Final Office Action mailed Jan. 20, 2010", 21 pgs.
"U.S. Appl. No. 10/525,736, Non Final Office Action mailed Feb. 13, 2014", 20 pgs.
"U.S. Appl. No. 10/525,736, Non Final Office Action mailed Aug. 5, 2011", 20 pgs.
"U.S. Appl. No. 10/525,736, Non Final Office Action mailed Nov. 14, 2008", 18 pgs.
"U.S. Appl. No. 10/525,736, Notice of Allowance mailed Oct. 10, 2014", 11 pgs.
"U.S. Appl. No. 10/525,736, Response filed Feb. 13, 2009 to Non Final Office Action mailed Nov. 14, 2008", 16 pgs.

(Continued)

*Primary Examiner* — Samira Jean-Louis
(74) *Attorney, Agent, or Firm* — Schwegman Lundberg & Woessner, P.A.

(57) ABSTRACT

This invention relates to pharmaceutical products and compositions for use in the treatment of asthma and related disorders, and especially but not exclusively for the treatment of chronic obstructive pulmonary disease (COPD). More particularly, the invention provides pharmaceutical products and compositions comprising specific anticholinergic agents, β-2 agonists and corticosteroids.

10 Claims, No Drawings

(56) References Cited

OTHER PUBLICATIONS

"U.S. Appl. No. 10/525,736, Response filed Mar. 28, 2011 to Final Office Action mailed Sep. 30, 2010", 24 pgs.
"U.S. Appl. No. 10/525,736, Response filed Jul. 20, 2010 to Non Final Office Action mailed Jan. 20, 2010", 17 pgs.
"U.S. Appl. No. 10/525,736, Response filed Aug. 3, 2012 to Final Office Action mailed Feb. 3, 2012", 16 pgs.
"U.S. Appl. No. 10/525,736, Response filed Aug. 11, 2014 to Non Final Office Action mailed Feb. 13, 2014", 14 pgs.
"U.S. Appl. No. 10/525,736, Response filed Oct. 23, 2008 to Restriction Requirement mailed Sep. 23, 2008", 2 pgs.
"U.S. Appl. No. 10/525,736, Response filed Nov. 4, 2009 to Final Office Action mailed May 5, 2009", 13 pgs.
"U.S. Appl. No. 10/525,736, Response filed Nov. 30, 2011 to Non-Final Office Action mailed Aug. 5, 2011", 32 pgs.
"U.S. Appl. No. 10/525,736, Restriction Requirement mailed Sep. 23, 2008", 8 pgs.
"European Application Serial No. 10184354, European Search Report mailed Mar. 30, 2011", 2 pgs.
"European Application Serial No. 10184546, European Search Report mailed Mar. 30, 2011", 2 pgs.
"European Application Serial No. 10184579, European Search Report mailed Mar. 31, 2011", 4 pgs.
"European Application Serial No. 10184584, European Search Report mailed Mar. 30, 2011", 3 pgs.
"European Application Serial No. 10184597, European Search Report mailed Mar. 31, 2011", 2 pgs.
"European Application Serial No. 10184651, European Search Report mailed Apr. 1, 2011", 3 pgs.
Aziz, I, et al., "Comparative trough effects of formoterol and salmeterol on lymphocyte beta2-adrenoceptor—regulation and bronchodilation", Eur. J. Clin. Pharmacol., 55, (1999), 431-436.
Aziz, I., et al., "A Bolus of Inhaled Budesonide Rapidly Reverses Airway Subsensitivity and beta2-Adrenoceptor Down-regulation After Regular Inhaled Formoterol", Chest, 115, (Mar. 1999), 623-628.
Aziz, Imran, et al., "Effects of Once-Daily Formoterol and Budesonide Given Alone or in Combination on Surrogate Inflammatory Markers in Asthmatic Adults", Chest, 118, (Oct. 2000), 1049-1058.
Bateman, E. D., et al., "Salmeterol/Fluticasone Combination Inhaler: A New, Effective and Well Tolerated Treatment for Asthma", Clin. Drug Invest., 16, (Sep. 1998), 193-201.
Dissanayake, et al., "Respiratory Medicine", (2012), S20-S28.
Finlay, et al., "The Mechanics of Inhaled Pharmaceuticals Aerosols", Chapter 7, (2001), 119-174.
Finlay, W. H, "Chapter 4—Particle size changes due to evaporation or condensation", The Mechanics of Inhaled Pharmaceutical Aerosols : an introduction, (2001), 47-91.
Foulds, R. A, et al., "Comparison of lung deposition of a solution after nebulization by three commonly used portable nebulizers", Pharmaceutisch Weekblad Scientific Edition, vol. 5, (1983), 74-76.
Gupta, R. K., et al., "An Evaluation of Salmeterol in the treatment of Chronic Obstructive Pulmonary Diseases", The Indian Journal of Chest Disease & Allied Sciences, vol. 44, No. 3, (2002), 165-172.
Harbison, S. J., et al., "Possible steroid-sparing effect in asthma of lyprinol, a shellfish lipid extract", The Medical Journal of Australia, 173, (Nov. 20, 2000), p. 560.
Kizer, K. M, et al., "Blurred vision from ipratropium bromide inhalation", Am. J. Health-Syst. Pharm., 56, (May 1, 1999), 914-915.
Lipworth, B. J, et al., "Effects of Adding a Leukotriene Antagonist or a Long-Acting Beta2-Agonist in Asthmatic Patients with the Glycine-16 Beta2-Adrenoceptor Genotype", The American Journal of Medicine, 109, (Aug. 1, 2000), 114-121.
Miravitlles, M., "Treatment and quality of life in patients with chronic obstructive disease", Quality of Life research, vol. 11, No. 4, (2002), 329-338.
Parameswaran, K., et al., "Sputum eosinophil count to assess compliance with corticosteroid therapy in asthma", J Allergy Clin Immunol. 1999;104, 502-503.
Smeenk, F.W.J.M., et al., "Opportunistic lung infections in patients with chronic obstructive pulmonary disease: a side effect of inhaled corticosteroids?", Ned. Tijdschr. Geneeskd., 140, Abstract Only, Retrieved from STN Database, Accession No. 1996-09890, (1996), 1 pg.

PHARMACEUTICAL PRODUCTS AND COMPOSITION COMPRISING SPECIFIC ANTICHOLINERGIC AGENTS, β-2 AGONISTS AND CORTICOSTEROIDS

CROSS-REFERENCE TO RELATED APPLICATION

This application is a divisional of U.S. patent application Ser. No. 10/525,736, filed Jun. 6, 2005, which claims priority under 35 U.S.C. §371 of PCT/GB2003/003751, filed Aug. 29, 2003 and published as WO 2004/019985 A1, on Mar. 11, 2004, which application, claims priority under Title 35 U.S.C. §119 to United Kingdom Patent Application No.02273423, filed on Nov. 22, 2002 and to United Kingdom Patent Application No. 02200954, filed Aug. 29, 2002, which applications and publication are incorporated herein by reference in their entirety.

This invention relates to pharmaceutical products and compositions for use in the treatment of asthma and related disorders, and especially but not exclusively for the treatment of chronic obstructive pulmonary disease (COPD).

The pathophysiology of asthma and related disorders involves various distinct symptoms, including bronchoconstriction, inflammation of the airways, and increased mucous secretion, which results in wheezing, coughing and shortness of breath. A persistent or recurrent cough may exacerbate the problem by causing further irritation and inflammation of the airways. The causes of asthma are wide-ranging and not yet fully understood.

Bronchoconstriction occurs due to bronchial smooth muscle spasm and airway inflammation with mucosal edema. Asthma and other related disorders, have been known to be treated with β-2 adrenergic receptor agonists (β-2 agonist) as they provide a bronchodilator effect to the patients, resulting in relief from the symptoms of breathlessness. β-2 Agonists can be short acting for immediate relief, or long acting for long-term prevention, of asthma symptoms. Short acting β-2 agonists currently available include: salbutamol, biltolterol, pirbuterol and terbutaline. Long acting β-2 agonists currently available include salmeterol and formoterol.

Whilst it is also known that β-2 agonists provide symptomatic relief of bronchoconstriction in patients, another component of asthma, i.e. inflammation, often requires separate treatment. Typically this involves treatment with a steroid. Indeed, treatment with a corticosteroid is considered one of the most potent and effective therapies currently available for persistent asthma. Currently available corticosteroids include: beclomethasone, budesonide, flunisolide, fluticasone, mometasone and triamcinolone.

Bronchoconstriction and inflammation are also associated with bronchial plugging with secretions, which may be treated with anti-cholinergic agents, such as troventol, ipratropium, oxitropium and tiotropium.

These medicaments can be administered in different ways, such as in MDIs (metered-dosage inhalers), in DPIs (dry powder inhalers), and in oral and liquid formulations. Treatment in these different ways calls for the patient to comply with different dosage regimens, different frequencies of administration, etc. Also, since most of the medications are in the form of aerosols, the patient is required to carry several formulations and dispensers, one for each of these medicaments.

To assist patient compliance, combination products are known, e.g. an inhalation combination medication of fluticasone propionate and salmeterol, the combination being provided in one easy-to-use device. This combination product provides simultaneous treatment of airway constriction by means of the β-2 agonist (salmeterol), and treatment of inflammation by means of the steroid (fluticasone propionate).

A combination of ipratropium bromide and salbutamol is also known. This combination therapy provides an anticholinergic (ipratropium bromide) to reduce the bronchial secretions and a β-2 agonist (salbutamol) to reduce constriction. Other described combinations include ipratropium and salbutamol (WO 01/76601) and tiotropium and formoterol (WO 00/47200).

It would be highly desirable, however, to provide a combination therapy suitable to reduce bronchial inflammation, bronchial constriction and bronchial secretions in a single product or dosage form. It would also be desirable to provide such a combination product or composition in a form whereby the correct dosage of the various components is easily and safely administered.

We have now found that certain therapeutic three-in-one combinations comprising specific β-2 agonists, anti-cholinergics and steroids surprisingly provide an enhanced, synergistic, effect in terms of treatment of bronchoconstriction, inflammation and mucous secretions of airways. Also the three-in-one combination therapy as provided by the present invention is an extremely patient-friendly combination, which results in maximum patient compliance and better control of asthma than the known combinations or single therapies.

The present invention further provides, therefore, a pharmaceutical product comprising any one of the following combinations of therapeutic agents, as a combined preparation for simultaneous, separate or sequential use in the treatment of conditions for which administration of one or more of the therapeutic agents is indicated:
(i) salmeterol, ciclesonide and tiotropium;
(ii) formoterol, budesonide and ipratropium;
(iii) formoterol, ciclesonide and tiotropium;
(iv) formoterol, budesonide and oxitropium;
(v) salbutamol, beclomethasone and ipratropium;
(vi) salbutamol, budesonide and tiotropium;
(vii) terbutaline, fluticasone and tiotropium;
(viii) terbutaline, fluticasone and ipratropium;
(ix) salbutamol, budesonide and ipratropium;
(x) salmeterol, fluticasone and ipratropium;
(xi) salmeterol, budesonide and ipratropium;
(xii) salmeterol, fluticasone and tiotropium; and
(xiii) formoterol, budesonide and tiotropium.

It will also be appreciated from the above, that the respective therapeutic agents of the combined preparations can be administered simultaneously, either in the same or different pharmaceutical formulations, or separately or sequentially. If there is separate or sequential administration, it will also be appreciated that the subsequently administered therapeutic agents should be administered to a patient within a time scale so as to achieve, or more particularly optimise, the above referred to advantageous synergistic therapeutic effect of a combined preparation as present in a pharmaceutical product according to the present invention.

The present invention also provides a pharmaceutical composition comprising any one of the following combinations of therapeutic agents:
(i) salmeterol, ciclesonide and tiotropium;
(ii) formoterol, budesonide and ipratropium;
(iii) formoterol, ciclesonide and tiotropium;
(iv) formoterol, budesonide and oxitropium;
(v) salbutamol, beclomethasone and ipratropium;

(vi) salbutamol, budesonide and tiotropium;
(vii) terbutaline, fluticasone and tiotropium;
(viii) terbutaline, fluticasone and ipratropium;
(ix) salbutamol, budesonide and ipratropium;
(x) salmeterol, fluticasone and ipratropium;
(xi) salmeterol, budesonide and ipratropium;
(xii) salmeterol, fluticasone and tiotropium; and
(xiii) formoterol, budesonide and tiotropium.
together with a pharmaceutically acceptable carrier or excipient therefor.

The abovementioned compounds may exist, and be used in the present invention, in various active forms, whilst retaining the same physiological function. For example, the anticholinergic agents, β-2 agonists and corticosteroids may exist as various acid addition salts, such as those formed from hydrochloric, hydrobromic, sulphuric, acetic, lactic, maleic, tartaric, oxalic, methanesulphonic, p-toluenesulphonic and benzenesulphonic acids. The skilled person will also appreciate that the abovementioned compounds may also exist as esters and (R) and (S) enantiomers and provided the desired activity is maintained, they may be used in the present invention.

Specific triple combinations of the invention as illustrated by the Examples are:
(i) salmeterol, ciclesonide and tiotropium bromide;
(ii) formoterol, budesonide and ipratropium;
(iii) formoterol, ciclesonide and tiotropium bromide;
(iv) formoterol, budesonide and oxitropium;
(v) salbutamol sulphate, beclomethasone and ipratropium;
(vi) salbutamol sulphate, budesonide and tiotropium bromide;
(vii) terbutaline sulphate, fluticasone and tiotropium bromide;
(viii) terbutaline sulphate, fluticasone and ipratropium bromide;
(ix) salbutamol sulphate, budesonide and ipratropium bromide;
(x) salmeterol, fluticasone propionate and ipratropium bromide;
(xi) salmeterol, budesonide and ipratropium bromide;
(xii) salmeterol, fluticasone propionate and tiotropium bromide; and
(xiii) formoterol, budesonide and tiotropium bromide.

The pharmaceutical composition may be provided in any suitable dosage form. Preferably the composition is in the form of a suspension, a particulate suspension or a clear solution. The pharmaceutical composition of the present invention may alternatively be provided as an inhalation powder.

The pharmaceutical composition of the present invention may be administered by any suitable administration method and it may be preferred that the composition is administered as an aerosol. The composition of the present invention can comprise a propellant-containing dosage aerosol, an inhalation powder or a propellant free inhalation solution or suspension. The compositions of the present invention may thus be provided by, for example, a metered dose inhaler (MDI), dry powder inhaler (DPI), nebules, nebuliser or nasal spray.

In the case of a propellant-containing dosage aerosol, typically the propellant can be selected from the group consisting of 1,1,1,2-tetrafluoroethane, 1,1,1,2,3,3,3-heptafluoroethane, monofluorotrichloromethane and dichlorodifluoromethane.

In the case of a particulate suspension or a solution for the propellant-containing aerosol composition, the composition may further comprise one or more co-solvents. The composition may comprise both a propellant and a co-solvent, in which case it is desirable that the co-solvent has a greater polarity than the propellant. The co-solvent used may be any suitable solvent. Typically the co-solvent is ethanol. Generally the ratio of propellant to solvent is between 50:50 to 99:1.

If aerosolized, the formulation may consist of a surface-active agent to stabilize the formulation and for the lubrication of a valve system in the inhaler/nebuliser/nasal spray.

Some of the most commonly used surface-active agents in the aerosol formulations are oils derived from natural sources, such as corn oil, olive oil, cotton seed oil and sunflower seed oil and phospholipids. Preferred surfactants for use according to the present invention are oleic acid, lecithin or sorbitol trioleate. In these embodiments, the surface-active agents are preferably used in the formulations in the ratio of 0.00002 wt % wt to 20 wt % of the active ingredients. The surface-active agents may exceed this weight ratio in cases where drug concentration in the formulation is very low.

The active ingredients in all the above aerosol formulations are preferably in the concentration of 0.001 wt % to 5 wt % of the total formulation.

The active ingredients are provided in an appropriate particle size, generally in the range from nano-size to about 12 μm. Preferably, approximately 95% are below 5 or 6 μm (micrometers), with the all particles being below 12 μm (when measured by laser), or approximately 95% below 2.5 μm and the rest of the particles between 2.5-5 μm (when measured by microscope).

According to another aspect of the invention there is provided an aerosol device, comprising a housing containing a composition as described above, and a dispensing mechanism for dispensing the composition from the housing in a metered dose.

The dispensing mechanism may include a valve capable of releasing a metered dosage of the composition. Preferably the housing is sealed and pressurized at a pressure exceeding atmospheric pressure.

The housing may be metallic, preferably aluminum. Preferably, the housing is plastic-coated, lacquer-coated or anodised. The composition of the present invention may be placed in the housing through a suitable metering device.

Preferred combinations of active ingredients for administration by way of a propellant-containing dosage aerosols according to the present invention are further illustrated by the Examples and can include any one of the following combinations:
(i) salmeterol, ciclesonide and tiotropium;
(ii) formoterol, budesonide and ipratropium;
(iii) formoterol, ciclesonide and tiotropium;
(iv) formoterol, budesonide and oxitropium;
(v) salbutamol, beclomethasone and ipratropium;
(vi) salbutamol, budesonide and tiotropium;
(vii) terbutaline, fluticasone and tiotropium;
(viii) salmeterol, fluticasone and tiotropium; and
(ix) formoterol, budesonide and tiotropium.

More specifically the following may be administered by way of propellant-containing dosage aerosols according to the present invention:
(i) salmeterol, ciclesonide and tiotropium bromide;
(ii) formoterol, budesonide and ipratropium;
(iii) formoterol, ciclesonide and tiotropium bromide;
(iv) formoterol, budesonide and oxitropium;
(v) salbutamol sulphate, beclomethasone and ipratropium;

(vi) salbutamol sulphate, budesonide and tiotropium bromide;
(vii) terbutaline sulphate, fluticasone and tiotropium bromide;
(viii) salmeterol, fluticasone propionate and tiotropium bromide;
(ix) formoterol, budesonide and tiotropium bromide.

In the case where the triple combinations of the present invention are provided as inhalation powders, typically suitable pharmaceutically acceptable excipients may be selected from monosaccharides, disaccharides, oligosaccharides, polysaccharides or the like, with the use of lactose as the excipient in the inhalation powders of the present invention being preferred. The inhalation powders of the present invention can typically be administered by means of dry powder inhalers known in the art. Preferred combinations of active ingredients for administration by way of inhalation powders according to the present invention are further illustrated by the Examples and can include any one of the following combinations:

(i) salmeterol, ciclesonide and tiotropium;
(ii) formoterol, budesonide and ipratropium;
(iii) formoterol, ciclesonide and tiotropium;
(iv) salbutamol, beclomethasone and ipratropium;
(v) salbutamol, budesonide and tiotropium; and
(vi) terbutaline, fluticasone and tiotropium.

More specifically the following may be administered by way of inhalation powders according to the present invention:

(i) salmeterol, ciclesonide and tiotropium bromide;
(ii) formoterol, budesonide and ipratropium;
(iii) formoterol, ciclesonide and tiotropium bromide;
(iv) salbutamol sulphate, beclomethasone and ipratropium;
(v) salbutamol sulphate, budesonide and tiotropium bromide; and
(vi) terbutaline sulphate, fluticasone and tiotropium bromide.

The propellant free inhalation solutions of the present invention are typically suitable for administration by way of nebulisation, employing nebulisers well known in the art that can advantageously be employed to produce inhalable aerosols comprising the triple combinations of active ingredients according to the present invention. Preferred combinations of active ingredients for administration by way of propellant free inhalation solutions according to the present invention are further illustrated by the Examples and can include any one of the following combinations:

(i) terbutaline, fluticasone and ipratropium;
(ii) salbutamol, budesonide and ipratropium;
(iii) salmeterol, fluticasone and ipratropium; and
(iv) salmeterol, budesonide and ipratropium.

More specifically the following may be administered by way of propellant free inhalation solutions according to the present invention:

(i) terbutaline sulphate, fluticasone and ipratropium bromide;
(ii) salbutamol sulphate, budesonide and ipratropium bromide;
(iii) salmeterol, fluticasone propionate and ipratropium bromide; and
(iv) salmeterol, budesonide and ipratropium bromide.

According to another aspect of the invention, there is provided the use of any one of the following combinations in the manufacture of a medicament for the prophylaxis or treatment of conditions for which administration of one or more of the therapeutic agents is indicated:

(i) salmeterol, ciclesonide and tiotropium;
(ii) formoterol, budesonide and ipratropium;
(iii) formoterol, ciclesonide and tiotropium;
(iv) formoterol, budesonide and oxitropium;
(v) salbutamol, beclomethasone and ipratropium;
(vi) salbutamol, budesonide and tiotropium;
(vii) terbutaline, fluticasone and tiotropium;
(viii) terbutaline, fluticasone and ipratropium;
(ix) salbutamol, budesonide and ipratropium;
(x) salmeterol, fluticasone and ipratropium;
(xi) salmeterol, budesonide and ipratropium;
(xii) salmeterol, fluticasone and tiotropium; and
(xiii) formoterol, budesonide and tiotropium.

The triple combinations as provided by the present invention are useful for the treatment of inflammatory or respiratory tract diseases, especially asthma and/or chronic obstructive pulmonary disease (COPD), by simultaneous or successive administration.

According to another aspect of the invention there is provided a method for the prophylaxis or treatment of inflammatory or respiratory tract diseases, said method comprising administering either sequentially or simultaneously, to a patient in need thereof, a therapeutically effective amount of any one of the following combinations:

(i) salmeterol, ciclesonide and tiotropium;
(ii) formoterol, budesonide and ipratropium;
(iii) formoterol, ciclesonide and tiotropium;
(iv) formoterol, budesonide and oxitropium;
(v) salbutamol, beclomethasone and ipratropium;
(vi) salbutamol, budesonide and tiotropium;
(vii) terbutaline, fluticasone and tiotropium;
(viii) terbutaline, fluticasone and ipratropium;
(ix) salbutamol, budesonide and ipratropium;
(x) salmeterol, fluticasone and ipratropium;
(xi) salmeterol, budesonide and ipratropium;
(xii) salmeterol, fluticasone and tiotropium; and
(xiii) formoterol, budesonide and tiotropium.

Any of the following specific triple combinations of the invention as illustrated by the Examples are suitable to be employed in the manufacture of a medicament, or a method of treatment, as referred to above:

(i) salmeterol, ciclesonide and tiotropium bromide;
(ii) formoterol, budesonide and ipratropium;
(iii) formoterol, ciclesonide and tiotropium bromide;
(iv) formoterol, budesonide and oxitropium;
(v) salbutamol sulphate, beclomethasone and ipratropium;
(vi) salbutamol sulphate, budesonide and tiotropium bromide;
(vii) terbutaline sulphate, fluticasone and tiotropium bromide;
(viii) terbutaline sulphate, fluticasone and ipratropium bromide;
(ix) salbutamol sulphate, budesonide and ipratropium bromide;
(x) salmeterol, fluticasone propionate and ipratropium bromide;
(xi) salmeterol, budesonide and ipratropium bromide;
(xii) salmeterol, fluticasone propionate and tiotropium bromide; and
(xiii) formoterol, budesonide and tiotropium bromide.

These products or compositions as provided by the present invention are especially useful in the treatment of COPD. They will normally be administered by inhalation, once or twice daily. By way of example, a preferred dosage for twice daily administrations would be:

a) formoterol (6 mcg)/budesonide (200 mcg)/ipratropium (40 mcg)

b) formoterol (6 mcg)/budesonide (200 mcg)/oxitropium (200 mcg).

The invention will now be described with reference to the following examples, which do not limit the scope of the invention in any way.

EXAMPLE 1

|  | Per aerosol housing |
|---|---|
| Tiotropium bromide | 2.4 mg |
| Salbutamol | 24 mg |
| Budesonide | 24 mg |
| 1,1,1,2-Tetrafluoroethane | 18.2 gms |

EXAMPLE 2

|  | Per aerosol housing |
|---|---|
| Tiotropium bromide | 2.4 mg |
| Terbutaline Sulphate | 60 mg |
| Fluticasone | 12 mg |
| 1,1,1,2-Tetrafluoroethane | 18.2 gms |

In the above formulations (Examples 1 and 2), the active ingredients were initially weighed in an aluminum can. Then a metering valve was placed on the can and crimped with a vacuum crimper and then the propellant HFA 134a was charged through the metering valve.

EXAMPLE 3

|  | Per aerosol housing |
|---|---|
| Tiotropium bromide | 2.4 mg |
| Salbutamol | 24 mg |
| Budesonide | 24 mg |
| Ethanol | 2.73 gms |
| 1,1,1,2-Tetrafluoroethane | 15.47 gms |

In the above formulation the active ingredients were first weighed in an aluminum can, then the ethanol was added and the solution was sonicated for 5 min. The metering valve was placed on the can and crimped with a vacuum crimper, and then propellant HFA 134a was charged through the metering valve.

EXAMPLE 4

|  | Per aerosol housing |
|---|---|
| Tiotropium bromide | 2.4 mg |
| Salbutamol | 24 mg |
| Budesonide | 24 mg |
| Ethanol | 2.73 gms |
| Oleic acid (10%) | 5.04 mg |
| 1,1,1,2-Tetrafluoroethane | 15.47 gms |

In the above formulation the active ingredients were first weighed in an aluminum can then the ethanol and the surfactant were added and solution was sonicated for 5 min. The metering valve was placed on the can and crimped with a vacuum crimper and then the HFA 134a was charged through the metering valve.

EXAMPLE 5

|  | Per aerosol housing |
|---|---|
| Tiotropium bromide | 2.4 mg |
| Terbutaline Sulphate | 60 mg |
| Fluticasone | 12 mg |
| Ethanol | 0.364 gms |
| 1,1,1,2-Tetrafluoroethane | 18.2 gms |

EXAMPLE 6

|  | Per aerosol housing |
|---|---|
| Tiotropium bromide | 2.4 mg |
| Terbutaline Sulphate | 60 mg |
| Fluticasone | 12 mg |
| Ethanol | 0.364 gms |
| Oleic acid (0.02%) | 0.014 mg |
| 1,1,1,2-Tetrafluoroethane | 17.83 gms |

The above formulations (Examples 5 and 6) were weighed in an aluminum can, and a metering valve was crimped on the can and the propellant added.

EXAMPLE 7

| Ingredients | Quantity (Per aerosol housing) |
|---|---|
| Tiotropium bromide | 1.8 mg |
| Salmeterol | 5.81 mg |
| Ciclesonide | 8.0 mg |
| 1,1,1,2-Tetrafluoroethane | 12.2 g |

The active ingredients were initially weighed in an aluminum can. The metering valve was then placed on the can and crimped with a vacuum crimper and then the propellant HFA134a was charged through the metering valve.

EXAMPLE 8

| Ingredients | Quantity (Per aerosol housing) |
|---|---|
| Tiotropium bromide | 1.8 mg |
| Salmeterol | 5.81 mg |
| Ciclesonide | 8.0 mg |
| Ethanol (2%) | 0.244 g |
| 1,1,1,2-Tetrafluoroethane | 12 g |

The active ingredients were initially weighed in an aluminum can, then ethanol was added and the solution was sonicated for 5 minutes. The metering valve was placed on the can and crimped with a vacuum crimper and then the propellant HFA134a was charged through the metering valve.

EXAMPLE 9

| Ingredients | Quantity (Per aerosol housing) |
| --- | --- |
| Tiotropium bromide | 1.8 mg |
| Salmeterol | 5.81 mg |
| Ciclesonide | 8.0 mg |
| Ethanol (2%) | 0.244 g |
| Oleic acid (0.02%) | 0.003 mg |
| 1,1,1,2-Tetrafluoroethane | 12 g |

The active ingredients were initially weighed in an aluminum can, then ethanol and oleic acid were added and the solution was sonicated for 5 minutes. The metering valve was placed on the can and crimped with a vacuum crimper and then the propellant HFA134a was charged through the metering valve.

EXAMPLE 10

| Ingredients | Quantity (Per aerosol housing) |
| --- | --- |
| Formoterol | 1 mg |
| Ipratropium | 3.2 mg |
| Budesonide | 8.0 mg |
| 1,1,1,2-Tetrafluoroethane | 12.2 g |

The active ingredients were initially weighed in an aluminum can. The metering valve was then placed on the can and crimped with a vacuum crimper and then the propellant HFA134a was charged through the metering valve.

EXAMPLE 11

| Ingredients | Quantity (Per aerosol housing) |
| --- | --- |
| Formoterol | 1 mg |
| Ipratropium | 3.2 mg |
| Budesonide | 8.0 mg |
| Ethanol (15%) | 1.83 g |
| 1,1,1,2-Tetrafluoroethane | 18.2 g |

The active ingredients were initially weighed in an aluminum can, then ethanol was added and the solution was sonicated for 5 minutes. The metering valve was placed on the can and crimped with a vacuum crimper and then the propellant HFA134a was charged through the metering valve.

EXAMPLE 12

| Ingredients | Quantity (Per aerosol housing) |
| --- | --- |
| Formoterol | 1.0 mg |
| Ipratropium | 3.2 mg |
| Budesonide | 8.0 mg |
| Ethanol | 1.83 g |
| Lecithin (1%) | 0.122 mg |
| 1,1,1,2-Tetrafluoroethane | 18.2 g |

The active ingredients were initially weighed in an aluminum can, then ethanol and lecithin were added and the solution was sonicated for 5 minutes. The metering valve was placed on the can and crimped with a vacuum crimper and then the propellant HFA134a was charged through the metering valve.

EXAMPLE 13

| Ingredients | Quantity (Per aerosol housing) |
| --- | --- |
| Tiotropium Bromide | 1.8 mg |
| Formoterol | 1.0 mg |
| Ciclesonide | 8.0 mg |
| 1,1,1,2-Tetrafluoroethane | 12.2 g |

The active ingredients were initially weighed in an aluminum can. The metering valve was then placed on the can and crimped with a vacuum crimper and then the propellant HFA134a was charged through the metering valve.

EXAMPLE 14

| Ingredients | Quantity (Per aerosol housing) |
| --- | --- |
| Tiotropium Bromide | 1.8 mg |
| Formoterol | 1.0 mg |
| Ciclesonide | 8.0 mg |
| Ethanol (15%) | 1.83 g |
| 1,1,1,2-Tetrafluoroethane | 10.4 g |

The active ingredients were initially weighed in an aluminum can, then ethanol was added and the solution was sonicated for 5 minutes. The metering valve was placed on the can and crimped with a vacuum crimper and then the propellant HFA134a was charged through the metering valve.

EXAMPLE 15

| Ingredients | Quantity (Per aerosol housing) |
| --- | --- |
| Tiotropium Bromide | 1.8 mg |
| Formoterol | 1.0 mg |
| Ciclesonide | 8.0 mg |
| Ethanol | 1.83 g |
| Lecithin (1%) | 0.10 mg |
| 1,1,1,2-Tetrafluoroethane | 10.4 g |

The active ingredients were initially weighed in an aluminum can, then ethanol and lecithin were added and the solution was sonicated for 5 minutes. The metering valve was placed on the can and crimped with a vacuum crimper and then the propellant HFA134a was charged through the metering valve.

EXAMPLE 16

| Ingredients | Quantity (Per aerosol housing) |
| --- | --- |
| Oxitropium | 4.8 mg |
| Formoterol | 1.0 mg |

-continued

| Ingredients | Quantity (Per aerosol housing) |
|---|---|
| Budesonide | 8.0 mg |
| 1,1,1,2-Tetrafluoroethane | 12.2 g |

The active ingredients were initially weighed in an aluminum can. The metering valve was then placed on the can and crimped with a vacuum crimper and then the propellant HFA134a was charged through the metering valve.

EXAMPLE 17

| Ingredients | Quantity (Per aerosol housing) |
|---|---|
| Oxitropium | 4.8 mg |
| Formoterol | 1.0 mg |
| Budesonide | 8.0 mg |
| Ethanol (15%) | 1.83 g |
| 1,1,1,2-Tetrafluoroethane | 10.4 g |

The active ingredients were initially weighed in an aluminum can, then ethanol was added and the solution was sonicated for 5 minutes. The metering valve was placed on the can and crimped with a vacuum crimper and then the propellant HFA134a was charged through the metering valve.

EXAMPLE 18

| Ingredients | Quantity (Per aerosol housing) |
|---|---|
| Oxitropium | 4.8 mg |
| Formoterol | 1.0 mg |
| Budesonide | 8.0 mg |
| Ethanol (15%) | 1.83 g |
| Lecithin (1%) | 0.138 mg |
| 1,1,1,2-Tetrafluoroethane | 10.4 g |

The active ingredients were initially weighed in an aluminum can, then ethanol and lecithin were added and the solution was sonicated for 5 minutes. The metering valve was placed on the can and crimped with a vacuum crimper and then the propellant HFA134a was charged through the metering valve.

EXAMPLE 19

| Ingredients | Quantity (Per aerosol housing) |
|---|---|
| Salbutamol sulphate | 28.8 mg |
| Beclomethasone | 12.0 mg |
| Ipratropium | 4.8 mg |
| 1,1,1,2-Tetrafluoroethane | 18.2 g |

The active ingredients were initially weighed in an aluminum can. The metering valve was then placed on the can and crimped with a vacuum crimper and then the propellant HFA134a was charged through the metering valve.

EXAMPLE 20

| Ingredients | Quantity (Per aerosol housing) |
|---|---|
| Salbutamol sulphate | 28.8 mg |
| Beclomethasone | 12.0 mg |
| Ipratropium | 4.8 mg |
| Ethanol (2.5%) | 0.455 g |
| 1,1,1,2-Tetrafluoroethane | 17.75 g |

The active ingredients were initially weighed in an aluminum can, then ethanol was added and the solution was sonicated for 5 minutes. The metering valve was placed on the can and crimped with a vacuum crimper and then the propellant HFA134a was charged through the metering valve.

EXAMPLE 21

| Ingredients | Quantity (Per aerosol housing) |
|---|---|
| Salbutamol sulphate | 28.8 mg |
| Beclomethasone | 12.0 mg |
| Ipratropium | 4.8 mg |
| Ethanol (2.5%) | 0.455 g |
| Oleic acid (0.02%) | 0.009 mg |
| 1,1,1,2-Tetrafluoroethane | 17.75 g |

The active ingredients were initially weighed in an aluminum can, then ethanol and oleic acid were added and the solution was sonicated for 5 minutes. The metering valve was placed on the can and crimped with a vacuum crimper and then the propellant HFA134a was charged through the metering valve.

EXAMPLE 22

| Ingredients | Quantity (Per aerosol housing) |
|---|---|
| Salbutamol sulphate | 28.8 mg |
| Tiotropium bromide | 2.7 mg |
| Budesonide | 12 mg |
| 1,1,1,2-Tetrafluoroethane | 18.2 g |

The active ingredients were initially weighed in an aluminum can. The metering valve was then placed on the can and crimped with a vacuum crimper and then the propellant HFA134a was charged through the metering valve.

EXAMPLE 23

| Ingredients | Quantity (Per aerosol housing) |
|---|---|
| Salbutamol sulphate | 28.8 mg |
| Tiotropium bromide | 2.7 mg |
| Budesonide | 12 mg |
| Ethanol (2%) | 0.364 g |
| 1,1,1,2-Tetrafluoroethane | 17.83 g |

The active ingredients were initially weighed in an aluminum can, then ethanol was added and the solution was sonicated for 5 minutes. The metering valve was placed on the can and crimped with a vacuum crimper and then the propellant HFA134a was charged through the metering valve.

EXAMPLE 24

| Ingredients | Quantity (Per aerosol housing) |
|---|---|
| Salbutamol sulphate | 28.8 mg |
| Tiotropium bromide | 2.7 mg |
| Budesonide | 12 mg |
| Ethanol (2%) | 0.364 g |
| Oleic acid (0.02%) | 0.0087 mg |
| 1,1,1,2-Tetrafluoroethane | 17.83 g |

The active ingredients were initially weighed in an aluminum can, then ethanol and oleic acid were added and the solution was sonicated for 5 minutes. The metering valve was placed on the can and crimped with a vacuum crimper and then the propellant HFA134a was charged through the metering valve.

EXAMPLE 25

| Ingredients | Quantity (Per aerosol housing) |
|---|---|
| Terbutaline sulphate | 40 mg |
| Tiotropium bromide | 1.8 mg |
| Fluticasone | 8.0 mg |
| 1,1,1,2-Tetrafluoroethane | 18.2 g |

The active ingredients were initially weighed in an aluminum can. The metering valve was then placed on the can and crimped with a vacuum crimper and then the propellant HFA134a was charged through the metering valve.

EXAMPLE 26

| Ingredients | Quantity (Per aerosol housing) |
|---|---|
| Terbutaline sulphate | 40 mg |
| Tiotropium bromide | 1.8 mg |
| Fluticasone | 8.0 mg |
| Ethanol | 2.73 g |
| 1,1,1,2-Tetrafluoroethane | 12.2 g |

The active ingredients were initially weighed in an aluminum can, then ethanol was added and the solution was sonicated for 5 minutes. The metering valve was placed on the can and crimped with a vacuum crimper and then the propellant HFA134a was charged through the metering valve.

EXAMPLE 27

| Ingredients | Quantity (Per aerosol housing) |
|---|---|
| Terbutaline sulphate | 40 mg |
| Tiotropium bromide | 1.8 mg |
| Fluticasone | 8.0 mg |
| Ethanol | 2.73 g |
| Lecithin | 1.38 mg |
| 1,1,1,2-Tetrafluoroethane | 15.83 g |

The active ingredients were initially weighed in an aluminum can, then ethanol and lecithin were added and the solution was sonicated for 5 minutes. The metering valve was placed on the can and crimped with a vacuum crimper and then the propellant HFA134a was charged through the metering valve.

EXAMPLE 28

| Ingredients | Quantity (Per aerosol housing) |
|---|---|
| Tiotropium bromide | 1.8 mg |
| Salmeterol | 5.81 mg |
| Fluticasone | 20.0 mg |
| 1,1,1,2-Tetrafluoroethane | 12.2 g |

The active ingredients were initially weighed in an aluminum can. Metering valve was then placed on the can and crimped with a vacuum crimper and then the propellant HFA134a was charged through the metering valve.

EXAMPLE 29

| Ingredients | Quantity (Per aerosol housing) |
|---|---|
| Tiotropium bromide | 1.8 mg |
| Salmeterol | 5.81 mg |
| Fluticasone | 20.0 mg |
| Ethanol (2%) | 0.244 g |
| 1,1,1,2-Tetrafluoroethane | 12 g |

The active ingredients were initially weighed in an aluminum can, then ethanol was added and the solution was sonicated for 5 minutes. The metering valve was placed on the can and crimped with a vacuum crimper and then the propellant HFA134a was charged through the metering valve.

EXAMPLE 30

| Ingredients | Quantity (Per aerosol housing) |
|---|---|
| Tiotropium bromide | 1.8 mg |
| Salmeterol | 5.81 mg |
| Fluticasone | 20.0 mg |
| Ethanol (2%) | 0.244 g |
| Oleic acid (0.02%) | 0.003 mg |
| 1,1,1,2-Tetrafluoroethane | 12 g |

The active ingredients were initially weighed in an aluminum can, then ethanol and the surfactant were added and the solution was sonicated for 5 minutes. The metering valve was placed on the can and crimped with a vacuum crimper and then the propellant HFA134a was charged through the metering valve.

EXAMPLE 31

| Ingredients | Quantity (Per aerosol housing) |
|---|---|
| Formoterol | 1 mg |
| Tiotropium Bromide | 1.8 mg |
| Budesonide | 8.0 mg |
| 1,1,1,2-Tetrafluoroethane | 12.2 g |

The active ingredients were initially weighed in an aluminum can. Metering valve was then placed on the can and crimped with a vacuum crimper and then the propellant HFA134a was charged through the metering valve.

EXAMPLE 32

| Ingredients | Quantity (Per aerosol housing) |
|---|---|
| Formoterol | 1 mg |
| Tiotropium Bromide | 1.8 mg |
| Budesonide | 8.0 mg |
| Ethanol (15%) | 1.83 g |
| 1,1,1,2-Tetrafluoroethane | 18.2 g |

The active ingredients were initially weighed in an aluminum can, then ethanol was added and the solution was sonicated for 5 minutes. The metering valve was placed on the can and crimped with a vacuum crimper and then the propellant HFA134a was charged through the metering valve.

EXAMPLE 33

| Ingredients | Quantity (Per aerosol housing) |
|---|---|
| Formoterol | 1.0 mg |
| Tiotropium Bromide | 1.8 mg |
| Budesonide | 8.0 mg |
| Ethanol | 1.83 g |
| Lecithin (1%) | 0.122 mg |
| 1,1,1,2-Tetrafluoroethane | 18.2 g |

The active ingredients were initially weighed in an aluminum can, then ethanol and the surfactant were added and the solution was sonicated for 5 minutes. The metering valve was placed on the can and crimped with a vacuum crimper and then the propellant HFA134a was charged through the metering valve.

The following Examples are inhalation powders suitable for DPIs, and were prepared by techniques well known in the art.

EXAMPLE 34

| Ingredients | Quantity (in mg per capsule) |
|---|---|
| Tiotropium bromide | 0.018 mg |
| Salmeterol | 0.050 mg |
| Ciclesonide | 0.1-0.4 mcg |
| Lactose | q.s. 5-25 mg |

EXAMPLE 35

| Ingredients | Quantity (in mg per capsule) |
|---|---|
| Formoterol | 0.025-0.4 mg |
| Ipratropium | 0.048 mg |
| Budesonide | 0.1-0.4 mg |
| Lactose | q.s. 5-25 mg |

EXAMPLE 36

| Ingredients | Quantity (in mg per capsule) |
|---|---|
| Tiotropium Bromide | 0.018 mg |
| Formoterol | 0.025-0.4 mg |
| Ciclesonide | 0.1-0.4 mg |
| Lactose | q.s. 5-25 mg |

EXAMPLE 37

| Ingredients | Quantity (in mg per capsule) |
|---|---|
| Salbutamol sulphate | 0.2 mg |
| Beclomethasone | 0.1-0.4 mg |
| Ipratropium | 0.048 mg |
| Lactose | q.s. 5-25 mg |

EXAMPLE 38

| Ingredients | Quantity (in mg per capsule) |
|---|---|
| Salbutamol sulphate | 0.2 mg |
| Tiotropium bromide | 0.018 mg |
| Budesonide | 0.1-0.4 mg |
| Lactose | q.s. 5-25 mg |

EXAMPLE 39

| Ingredients | Quantity (in mg per capsule) |
|---|---|
| Terbutaline sulphate | 0.1-0.2 mg |
| Tiotropium bromide | 0.018 mg |
| Fluticasone | 0.025-0.4 mg |
| Lactose | q.s. 5-25 mg |

The following Examples are for propellant free inhalation solutions, and were prepared by techniques well known in the art.

EXAMPLE 40

| Ingredients | Quantity (% w/v) |
|---|---|
| Terbutaline sulphate | 0.25 |
| Ipratropium bromide | 0.025 |
| Fluticasone | 0.025-0.1 |
| Polysorbat-80 | 0.1 |
| Sodium chloride | 0.9 |
| Anhydrous citric acid | q.s. to pH 4.5 |
| Water, purified | 100 ml |

EXAMPLE 41

| Ingredients | Quantity (% w/v) |
|---|---|
| Ipratropium bromide | 0.025 |
| Salbutamol sulphate | 0.125 |
| Budesonide | 0.05 |
| Polysorbat-80 | 0.1 |
| Sodium chloride | 0.9 |
| Water, purified | 100 ml |

EXAMPLE 42

| Ingredients | Quantity (% w/v) |
|---|---|
| Ipratropium bromide | 0.025 |
| Salmeterol | 0.005 |
| Fluticasone propionate | 0.025-0.1 |
| Polysorbat-80 | 0.1 |
| Sodium chloride | 0.9 |
| Water, purified | 100 ml |

EXAMPLE 43

| Ingredients | Quantity (% w/v) |
|---|---|
| Ipratropium bromide | 0.025 |
| Salmeterol | 0.005 |
| Budesonide | 0.05 |
| Polysorbat-80 | 0.1 |
| Sodium chloride | 0.9 |
| Water, purified | 100 ml |

The invention claimed is:

1. A pharmaceutical composition comprising any one of the following corribinations of therapeutic agents in a form suitable for administration by inhalation:
   (i) salmeterol, ciclesonide and tiotropium;
   (ii) formoterol, budesonide and ipratropium;
   (iv) formoterol, budesonide and oxitropium;
   (v) salbutamol, beclornethasone and ipratropium;
   (vi) salbutamol, budesonide and tiotropium;
   (vii) terbutaline, fluticasone and tiotropium;
   (viii) terbutaline, fluticasone and ipratropium;
   (ix) salbutamol, budesonide and ipratropium;
   (x) salmeterol, fluticasone and ipratropium;
   (xi) salmeterol, budesonide and ipratropium;
   (xii) sahrieterol, fluticasone and tiotropium; and
      wherein the therapeutic agents are each provided in particulate form, each of the therapeutic agents individually has a particle size from nano-size up to about 12 µm, and approximately 95% of the therapeutic agent particles have a particle size of below 5 µm or 6 µm; and
      wherein each of the therapeutic agents can optionally independently be present as a pharmaceutically acceptable salt or ester thereof, and each of the therapeutic agents can optionally independently be present in enantiornerically pure form or as a racemic mixture, together with a pharmaceutically acceptable carrier or excipient therefor.

2. A composition according to claim 1, wherein each of the therapeutic agents of the composition is present in an amount 0.001 wt % to 5 wt % based on the weight of the total composition.

3. A composition according to claim 1, which is an aerosol.

4. A composition according claim 3, which is a propellant free inhalation solution or suspension.

5. A composition according to claim 1, which is an inhalation powder.

6. A composition according to claim 5, which comprises lactose as the excipient.

7. A composition according to claim 1, in a form suitable for use with a nebuliser.

8. A metered dose inhaler which contains a composition as defined in claim 1.

9. A dry powder inhaler which contains a composition as defined in claim 1.

10. A nebuliser which contains a composition as defined in claim 1.

* * * * *

UNITED STATES PATENT AND TRADEMARK OFFICE
CERTIFICATE OF CORRECTION

PATENT NO. : 9,446,054 B2
APPLICATION NO. : 14/570679
DATED : September 20, 2016
INVENTOR(S) : Lulla et al.

Page 1 of 2

It is certified that error appears in the above-identified patent and that said Letters Patent is hereby corrected as shown below:

On the Title Page

Item (72), in "Inventors", in Column 1, Line 1, delete "Mumbai" and insert --Mumbai, Maharashtra--, therefor Item (72), in "Inventors", in Column 1, Line 2, delete "Mumbai" and insert --Mumbai, Maharashtra--, therefor Item (73), in "Assignee", in Column 1, Line 1, delete "Mumbai" and insert --Mumbai Central--, therefor Item (30), in "Foreign Application Priority Data", in Column 1, Line 1, delete "0220095.4" and insert --002200954--, therefor Item (30), in "Foreign Application Priority Data", in Column 1, Line 2, delete "0227342.3" and insert --02273423--, therefor On page 2, in Column 2, under "Other Publications", Line 31, after "obstructive", insert --pulmonary--, therefor In the Claims In Column 18, Line 3, in Claim 1, delete "corribinations" and insert --combinations--, therefor In Column 18, Line 7, in Claim 1, delete "(iv)" and insert --(iii)--, therefor In Column 18, Line 8, in Claim 1, delete "(v)" and insert --(iv)--, therefor In Column 18, Line 8, in Claim 1, delete "beclornethasone" and insert --beclomethasone--, therefor Signed and Sealed this
Twenty-sixth Day of June, 2018

Andrei Iancu
*Director of the United States Patent and Trademark Office*

CERTIFICATE OF CORRECTION (continued)
U.S. Pat. No. 9,446,054 B2

In Column 18, Line 9, in Claim 1, delete "(vi)" and insert --(v)--, therefor

In Column 18, Line 10, in Claim 1, delete "(vii)" and insert --(vi)--, therefor

In Column 18, Line 11, in Claim 1, delete "(viii)" and insert --(vii)--, therefor In Column 18, Line 12, in Claim 1, delete "(ix)" and insert --(viii)--, therefor In Column 18, Line 13, in Claim 1, delete "(x)" and insert --(ix)--, therefor In Column 18, Line 14, in Claim 1, delete "(xi)" and insert --(x)--, therefor In Column 18, Line 15, in Claim 1, delete "(xii)" and insert --(xi)--, therefor In Column 18, Line 15, in Claim 1, delete "sahrieterol," and insert --salmeterol,--, therefor In Column 18, Line 27, in Claim 1, delete "enantiornerically" and insert --enantiomerically--, therefor In Column 18, Line 36, in Claim 4, after "according", insert --to--, therefor